United States Patent [19]

Commarieu et al.

[11] Patent Number: 5,990,356
[45] Date of Patent: Nov. 23, 1999

[54] METHOD FOR PURIFYING DIMETHYL SULPHOXIDE (DMSO)

[75] Inventors: Annie Commarieu, Pau; Isabelle Bazin, Gan, both of France

[73] Assignee: Elf Acquitaine Production, France

[*] Notice: This patent is subject to a terminal disclaimer.

[21] Appl. No.: 09/068,504

[22] PCT Filed: Nov. 15, 1996

[86] PCT No.: PCT/FR96/01806

§ 371 Date: May 12, 1998

§ 102(e) Date: May 12, 1998

[87] PCT Pub. No.: WO97/19057

PCT Pub. Date: May 29, 1997

[30] Foreign Application Priority Data

Nov. 17, 1995 [FR] France .................................. 95 13641

[51] Int. Cl.⁶ .................................................. C07C 315/06
[52] U.S. Cl. ............................. 568/37; 210/660; 210/638
[58] Field of Search ............................. 568/37; 210/638, 210/660, 681, 687

[56] References Cited

U.S. PATENT DOCUMENTS

| | | |
|---|---|---|
| 2,366,007 | 12/1944 | D'Alelio . |
| 2,631,127 | 3/1953 | D'Alelio . |
| 2,645,621 | 7/1953 | D'Alelio . |
| 2,683,695 | 7/1954 | Dwyer . |
| 3,358,036 | 12/1967 | Morenberg . |
| 3,376,203 | 4/1968 | Lackey . |
| 4,108,866 | 8/1978 | Tramier . |
| 4,724,082 | 2/1988 | Boom . |
| 4,861,490 | 8/1989 | Morris . |
| 4,894,168 | 1/1990 | Holl . |
| 5,300,628 | 4/1994 | Honda . |
| 5,674,662 | 10/1997 | Szmanda . |

FOREIGN PATENT DOCUMENTS

| | | |
|---|---|---|
| 656879 | 6/1965 | Belgium . |
| 2 014 385 | 4/1970 | France . |

OTHER PUBLICATIONS

"Anion Exchange in Dimethyl Sulfoxide" Alan M. Phipps, *Anal. Chem.* 40(12):1769–1773 (1968).

"La purification du dimethylsulfoxide" Chaudron et al., *Chimie Analytique* 53(5):310–314 (1971).

International Search Report dated Feb. 4, 1997.

*Primary Examiner*—Gary Geist
*Assistant Examiner*—Jean F Vollano
*Attorney, Agent, or Firm*—Bell, Boyd & Lloyd

[57] ABSTRACT

This process consists in placing liquid DMSO with a low water content in contact with an ion exchange resin in —$SO_3H$ form, and then in separating the liquid from the resin.

The DMSO thus obtained has a content of iron cation tracer element of less than or equal to 1 ppb and a content of Na cation tracer element of less than or equal to 2 ppb.

6 Claims, No Drawings

METHOD FOR PURIFYING DIMETHYL SULPHOXIDE (DMSO)

FIELD OF THE INVENTION

The present invention relates to a process for the purification of dimethyl sulphoxide (DMSO) and to the DMSO thus purified.

BACKGROUND OF THE INVENTION

The DMSO currently available on the market is a product which is already of good purity. Its commercial specifications are generally:

purity: $\geq 99.7\%$ by chromatography acidity: $\leq 0.04$ mg KOH/g by potentiometry crystallization point: $\geq 18.2°$ C.

visual appearance: clear water content: $\leq 0.15\%$ by weight relative to the total weight colour (APHA): $\leq 10$ Patent application FR 2,014,385 describes a process for the preparation of purified DMSO. This process uses a cationic ion exchanger which can be regenerated by a treatment with acids. On the other hand, the DMSO treated with this ion exchanger has a very high water content. Furthermore, the examples indicate the use of a strongly basic resin of the Amberlite IR-A 400 or Merck III type for dimethyl sulphide/DMSO/10% sulphuric acid ternary mixtures, which possibly leads to the neutralization of the acidity but also the introduction of the counterion of the basic resin into the mixture thus treated. Indeed, in this process the purification appears to be afforded essentially by fractional distillation of an aqueous DMSO solution treated beforehand with one or more ion exchangers.

Analyses of traces of metals have now been carried out on several samples (1 to 6) of commercial DMSO, from different sources. These analyses are reported in Table I.

The sodium, iron, potassium, calcium, chromium, copper, nickel and zinc concentrations were measured by ICP (plasma-torch atomic emission spectrometry, Perkin Elmer machine, Optima 3000 model) and are expressed in ppb (1 ppb=1 part by weight per billion=1 μg per kg).

The list of metal elements featured in Table I is not exhaustive as regards the metal elements present in these samples.

TABLE 1

| Sample | Metal cations | | | | | | | |
|---|---|---|---|---|---|---|---|---|
| | Na | Fe | K | Ca | Cr | Cu | Ni | Zn |
| 1 | 40 | 13 | 60 | 20 | 2 | 10 | 8 | 10 |
| 2 | 39 | 60 | 3 | 13 | 13 | <2 | 18 | 3 |
| 3 | 30 | 40 | 3 | 20 | 12 | <2 | 15 | 3 |
| 4 | 30 | 40 | 3 | 14 | 13 | <2 | 15 | 3 |
| 5 | 30 | <1 | 20 | 25 | <2 | <2 | <3 | <3 |
| 6 | 70 | 90 | 65 | 55 | 15 | 2 | 25 | 60 |
| Detection limit | 2 | 1 | 3 | 2 | 2 | 2 | 3 | 3 |

For certain applications such as, for example, in electronics or in pharmacy, the DMSOs analysed above contain too many metal impurities. In general, a DMSO containing less than 10 ppb of each alkali metal and alkaline-earth metal contaminant would be necessary for most of the uses in the two abovementioned technical fields.

DESCRIPTION OF THE INVENTION

The aim of the present invention is to find a process for the purification of commercial DMSO which is already of good purity but which is, however, of insufficient purity for certain applications.

This aim is achieved by a process for the purification of dimethyl sulphoxide (DMSO) in order to decrease the content of cations other than $H^+$ therein, characterized in that it includes the following steps:

1) a DMSO in the liquid state and with a low water content is selected, 2) this DMSO is placed in contact with a solid consisting of an ion exchange resin of sulphonic type having its active groups in sulphonic acid ($SO_3H$) form, 3) the liquid consisting of the purified DMSO with very low contents of cations other than $H^+$ is then separated from the solid by any suitable known means, in particular filtration, percolation or centrifugation.

Advantageously, the DMSO selected in step 1) has a water content of less than or equal to 0.15% by weight relative to the total weight.

Ion exchange by the use of resins is a very widely used technique for aqueous media and makes it possible in particular to obtain deionised water. The exchange of anions in liquid DMSO medium with a low water content has already been performed by Alan M. Phipps, Anal. Chem. 40(12) pp. 1769–1773, 1968, for the purpose of measuring the amounts of anions bound to the resin under experimental conditions approaching thermodynamic equilibrium.

We have found in the present invention that any cation $M^{n+}$ (n being an integer greater than or equal to 1) is retained and exchanged by $n.H^+$ protons by a sulphonic resin in protonic form, working with DMSO which has a low water content or is virtually anhydrous.

Preferably, the sulphonic resin is based on a polystyrene-divinylbenzene copolymer. The reason for this is that these resins have a skeleton which resists chemical attack and, in particular, they are not dissolved in DMSO which has a low water content or is virtually anhydrous. These resins are generally defined by their divinylbenzene content. Indeed, the latter determines the degree of crosslinking of the resin and thus the pore size in which the cationic exchange takes place at the atomic level.

Preferably, in the copolymer the divinylbenzene represents from 50 to 60% by weight and the polystyrene from 50 to 40% by weight relative to the total weight of the copolymer, without taking into account the sulphonic groups ($SO_3H$). This divinylbenzene content ensures good kinetic activity of the exchange of cations $M^{n+}$ by $n.H^+$.

The placing in contact at step 2) takes place at a temperature ranging from 18.45° C. (the melting point of DMSO) to 120° C. The temperature of 120° C. is the limit temperature of thermal stability of the resins.

Advantageously, the placing in contact of the DMSO in step 2) takes place at a temperature of from 19 to 80° C.

Preferably, this temperature ranges from 20 to 50° C. for DMSO.

To have a definition of the quality of the DMSO, which has low water content or is virtually anhydrous, that is capable of being obtained purified by the process according to the invention, iron and sodium have been selected as tracer and indicator elements of the general content of cations $M^+$, in particular alkali metal and alkaline-earth metal cations.

This DMSO is characterized in that it has a content of Fe cation tracer element of less than or equal to 1 ppb and a content of Na cation tracer element of less than or equal to 2 ppb, the respective detection limit of the method of analysis by plasma-torch atomic emission spectrometry.

EXAMPLES

The invention will be better understood with the aid of the following experimental section describing exemplary embodiments of the present invention.

Experimental section

I Reduction of the content of metals

I-1. Method of analysis:

Method of analysis of traces of metals in DMSO:

ICP (plasma-torch atomic emission spectrometry): the sample is introduced into a plasma torch, the various elements present are excited and emit photons whose energy is characteristic of the element since it is defined by the electronic structure of the element considered. We routinely used a Perkin Elmer machine (Optima 3000 model).

1-2. Methodology:

Principle: the traces of metals are in $M^{n+}$ form. By passing DMSO through a cation exchange resin, which is itself in $H^+$ form, the $M^{n+}$ ions are substituted in solution by $nH^{3o}$.

Since many cation exchange resins exist on the market, we chose to classify the resins according to their kinetic performance (batch reactions) and to test the most advantageous resins continuously. All the resins are:

in sulphonic form, based on poly(styrene-divinylbenzene), the initial content, before crosslinking, of divinylbenzene and the resin supplier being variable (see Table II), and in Table III:

in sulphonic form, based on poly(acrylic-divinylbenzene): C 106, in iminodiacetic form, based on poly(styrene-divinylbenzene): S 930, in aminophosphonic form, based on poly(styrene-divinylbenzene): S 940, in acetic form, based on poly(styrene-divinylbenzene)

1-3. Selection of the resins:

Principle: out of concern to simplify the analyses, sodium and/or iron were chosen as tracers representative of all of the metal impurities contained in the DMSO.

Sodium is characteristic of atmospheric and accidental pollution (dusts, environment) and iron is characteristic of the pollution which may arise in the process (stainless steel unit).

I-4. Reduction of the content of cations (other than $H^+$) in DMSO.

I-4-1. Batch treatment:

DMSO doped with 1000 ppb of iron and about 1000 ppb of sodium is placed in contact with a cation exchange resin, in $H^+$ form (2 g of resin per 100 g of DMSO in the form of a liquid) at 25° C. Samples of this liquid are taken over time. It is thus possible to monitor the change in iron and sodium concentrations over time.

All the resins are dried by placing them in suspension in methanol and evaporation under vacuum on a rotary evaporator (90° C., $20 \times 10^2$ Pa) until a constant weight is observed.

When the commercial resins are supplied in $H^+$ form, they are dried as they are.

When they are in $Na^{3o}$ form, they are exchanged beforehand to obtain the $H^+$ form in the following manner: 90 ml of resin are placed in a column. 540 ml of 5% HCl are passed through it at a constant flow rate and such that the operation lasts for 30 to 45 min. The resin is then rinsed with deionized water until the exiting water is neutral.

In certain cases (when a plateau is obtained in the case of the sodium concentration, at contents of the order of 200–300 ppb), the resins were exchanged again with 5% HCl.

Table II below collates, for each poly(styrene-divinylbenzene)-based sulphonic resin: the name of the supplier, the commercial reference of the resin, the divinylbenzene content and the iron and sodium contents of the DMSO as a function of time. The iron and sodium assays were performed by ICP. When the results are below the detection limit inherent in the machine, they are reported as "<detection limit" (1 ppb for iron and 2 ppb for sodium).

Table III collates the results obtained with DMSO placed in contact with other resins.

TABLE II

| | Example No. | | | | | |
|---|---|---|---|---|---|---|
| | 1 | 2 | 3 | 4 | 5 | 6 |
| | | | Supplier | | | |
| | Rohm & Haas | Rohm & Haas | Purolite | Purolite | Bayer | Bayer |
| | | | References | | | |
| | Amberlyst ® 35 | Amberlyst ® 36 | Hypersol Macronet ® MN 500 | Hypersol Macronet ® MN 500* | K 1221 | K 2631 |
| | | | % DVB | | | |
| | 20 | 12 | 60 | 60 | 4 | 12 |
| Time | Fe  Na | Fe  Na | Fe  Na | Fe  Na | Fe  Na | Fe  Na |
| 5 min. | 230  <2 | 400  200 | 300  540 | <1  23 | 800  700 | 380  220 |
| 10 min. | 200  <2 | 440  20 | 30  420 | <1  <2 | 200  800 | 170  <2 |
| 15 min. | 200  <2 | 440  <2 | <1  300 | <1  <2 | 300  400 | 170  <2 |
| 20 min. | 160  <2 | 380  <2 | <1  260 | <1  <2 | 300  160 | 160  <2 |

TABLE II-continued

| Time | Ex 1 Fe | Ex 1 Na | Ex 2 Fe | Ex 2 Na | Ex 3 Fe | Ex 4 Fe | Ex 4 Na | Ex 5 Fe | Ex 5 Na | Ex 6 Fe | Ex 6 Na |  |
|---|---|---|---|---|---|---|---|---|---|---|---|---|
| 25 min. | 160 | <2 | 370 | <2 | <1 | 260 | <1 | <2 | 400 | 170 | 170 | <2 |
| 30 min. | 150 | <2 | 360 | <2 | <1 | 240 | <1 | <2 | 400 | 80 | 180 | <2 |
| 45 min. | 160 | <2 | 360 | <2 | <1 | 240 | <1 | <2 | 120 | 90 | 170 | <2 |
| 60 min. | 150 | <2 | 300 | <2 | <1 | 220 | nd | nd | 60 | 40 | 160 | <2 |
| 90 min. | 160 | <2 | 260 | <2 | <1 | 220 | nd | nd | 40 | 20 | 180 | <2 |
| 120 min. | 160 | <2 | 200 | <2 | <1 | 220 | nd | nd | 40 | 20 | 180 | <2 |

| | Example No. | | | | |
|---|---|---|---|---|---|
| | 7 | 8 | 9 | 10 | 11 |
| Supplier | Mitsubishi | Mitsubishi | Rohm & Haas | Rohm & Haas | Rohm & Haas |
| References | Relite ®EXC04 | Relite ®EXC29 | XN 1010 | XN 1010* | Amberlyst ® 35 |
| % DVB | 60 | ? | 50 | 50 | 20 |

| Time | Fe | Na | Fe | Na | Fe | Na | Fe | Na | Fe | Na |
|---|---|---|---|---|---|---|---|---|---|---|
| 5 min. | 80 | 17 | 80 | 200 | 360 | 360 | 10 | 30 | 130 | 100 |
| 10 min. | 20 | <2 | 20 | 140 | 160 | 320 | 5 | 27 | 80 | 20 |
| 15 min. | 20 | <2 | 20 | 50 | 100 | 320 | <1 | 13 | 80 | 25 |
| 20 min. | 20 | <2 | 20 | 50 | 60 | 360 | <1 | 10 | 66 | 10 |
| 25 min. | 8 | <2 | 2 | 40 | 60 | 440 | <1 | <2 | 65 | <2 |
| 30 min. | <1 | <2 | 8 | 40 | 20 | 400 | <1 | <2 | 60 | <2 |
| 45 min. | <1 | <2 | 10 | 40 | nd | nd | nd | nd | nd | nd |
| 60 min. | <1 | <2 | 10 | 30 | nd | nd | nd | nd | nd | nd |
| 90 min. | <1 | <2 | nd | nd | nd | nd | nd | nd | nd | nd |
| 120 min. | <1 | <2 | 2 | 20 | nd | nd | nd | nd | nd | nd |

*resin exchanged again in the laboratory:
nd: not determined

TABLE III

| | Example No. | | | | |
|---|---|---|---|---|---|
| | 12 | 13 | 14 | 15 | 16 |
| Supplier | Purolite | Purolite | Purolite | Purolite | Purolite |
| References | MN 600 | C 160 | S930 | S940 | C106 |
| Ionic form | | Sulphonic | Iminodiacetic | Aminophosphonic | Carboxylic |
| Structure | Styrene-divinyl-benzene | Styrene-divinyl-benzene | Styrene-divinyl-benzene | Styrene-divinyl-benzene | Acrylic-divinyl-benzene |

| Time | Fe | Na | Fe | Na | Fe | Na | Fe | Na | Fe | Na |
|---|---|---|---|---|---|---|---|---|---|---|
| 0 min. | 1460 | 1330 | 1500 | 1400 | 1270 | 1360 | 1390 | 1330 | 1430 | 1350 |
| 30 min. | 800 | 1470 | 57 | 320 | 760 | 1260 | 64 | 1120 | 1430 | 1360 |
| 60 min. | 760 | 1460 | 37 | 380 | 600 | 1270 | <1 | 960 | 1430 | 1380 |
| 90 min. | 765 | 1500 | 37 | 400 | 460 | 1320 | <1 | 880 | 1160 | 1380 |
| 120 min. | 760 | 1500 | 37 | 400 | 430 | 1340 | <1 | 800 | 1090 | 1360 |

The preferred resins are those which, in the selection test I-3 above, lead in 30 min. to iron and sodium concentrations below or equal to the detection limits, i.e. 1 ppb for iron and 2 ppb for sodium.

Any resin not featured in Table II but which satisfies the criteria of test I-3 would also be preferred in the present invention.

On examining Table II, it may be seen that the resins Purolite MN 500*, Relite® EXCO4 and Rohm & Haas XN 1010* are the most active, and are consequently preferred. Their divinylbenzene percentage is from 50 to 60%.

I-4-2. Continuous treatment:

From the batch results, several continuous tests were carried out.

Test conditions: according to the rules commonly followed by those skilled in the art as regards the column diameter/grain size ratio, the column height/diameter ratio and the linear speed so as not to be diffusion-limited. The resin is suspended in 90 ml of DMSO in a beaker with gentle stirring (to remove the air bubbles) and this suspension is then introduced into a vertical polyethylene column whose lower part is fitted with a polyethylene sinter of porosity 70

μm. The beaker is rinsed with 10 ml of DMSO. Under the sinter, the column is fitted with a PTFE tap. This tap is closed during the filling operation. Once the resin has been loaded onto and packed in the column, the tap is opened and the column is fed continuously with DMSO by means of a pump fitted with a PTFE head. Samples are taken at regular intervals, either manually or using an automatic sampler. All the tubes and joints are made of PTFE. The flasks are made of high-density polyethylene.

I-4-2-1. Example 17

Relite® EXC04 resin

Volume of dry resin: 35 $cm^2$

Grain size: 0.3–0.8 mm

Column diameter: 1.5 cm

Bed height: 21 cm

Flow rate of DMSO: 0.35 l/h

Assay of iron and sodium in the samples by ICP.

Starting with a DMSO containing 10 ppb of sodium and 50 ppb of iron, 35 litres of DMSO containing less than 2 ppb of sodium and 1 ppb of iron (detection limits of each element by this technique) were obtained. The experiment was not continued to the saturation point of the resin.

I-4-2-2. Example 18

Relite® EXC29 resin

Volume of dry resin: 35 $cm^3$

Grain size: 0.3–0.8 mm

Column diameter: 1.5 cm

Bed height: 26 cm

Initial DMSO containing 40 ppb of sodium and 40 ppb of iron.

Flow rate of DMSO: 0.40 l/h

Assay of iron and sodium in the samples by ICP. See Table IV.

TABLE IV

| Volume of DMSO treated in litres | Na (ppb) | Fe (ppb) |
| --- | --- | --- |
| 0, (starting DMSO) | 40 | 40 |
| 1.46 | ≦2 | ≦1 |
| 4.06 | 25 | ≦1 |

I-4-2-3. Example 19

Hypersol Macronet® MN 500 resin

Volume of dry resin: 35 $cm^3$

Grain size: 0.3–1.2 mm

Column diameter: 1.5 cm

Bed height: 21 cm

Initial DMSO containing 25 ppb of sodium and 78 ppb of iron

Flow rate of DMSO: about 2 l/h iron and sodium in the samples by ICP.

The results are given in Table V below:

| Time in h | Volume treated in litres | Na in ppb | Fe in ppb |
| --- | --- | --- | --- |
| 0 | 0 | 25 | 78 |
| 104 | 208 | ≦2 | ≦1 |
| 120 | 240 | 20 | ≦1 |

I-4-2-4. Example 20

Relite® EXC04 resin

Volume of dry resin: 32 $cm^3$

Grain size: 0.3–0.8 mm

Column diameter: 1.5 cm

Bed height: 19 cm

Initial DMSO containing 20 ppb of sodium and 40 ppb of iron

Flow rate of DMSO: about 2 l/h

Assay of iron and sodium in the samples by ICP.

The results are given in Table VI below:.

| Time in h | Volume treated in litres | Na in ppb | Fe in ppb |
| --- | --- | --- | --- |
| 0 | 0 | 20 | 40 |
| 53 | 106 | ≦2 | ≦1 |
| 77 | 154 | ≦2 | ≦1 |

I-4-2-5. Examples 21 and 22.

Hypersol Macronet® MN 500 resin

Volume of dry resin: 31 $cm^3$

Grain size: 0.3–0.8 mm

Internal diameter of the column: 2 cm

Bed height: 10 cm

Initial DMSO: 10 ppb of sodium and 20 ppb of iron

DMSO flow rate: 3.14 l $h^{-1}$ (results—Table VII)

DMSO flow rate: 8.3 l $h^{-1}$ (results—Table VIII)

TABLE VII

| Equivalent volume 1 of DMSO/1 of resin* | Na ppb | Fe ppb |
| --- | --- | --- |
| 0 | <2 | <1 |
| 1700 | <2 | <1 |
| 2400 | <2 | <1 |
| 4100 | <2 | <1 |
| 7200 | <2 | 25 |
| 6948 | <2 | 26 |

*volume of DMSO treated per volume of resin, in litres.

TABLE VIII

| Equivalent volume 1 of DMSO/1 of resin* | Na ppb | Fe ppb |
| --- | --- | --- |
| 0 | <2 | <1 |
| 4887 | <2 | <1 |
| 6761 | <2 | 4 |
| 11313 | <2 | 5 |
| 13319 | 5 | 5 |
| 17806 | 18 | 24 |
| 19613 | 25 | 25 |

*volume of DMSO treated per volume of resin, in litres.

During these tests of Examples 21 and 22, it was verified that the calcium, zinc, magnesium and silicon contents were respectively less than 2, 2, 1 and 2 ppb.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the purification of dimethy sulphoxide (DMSO) to decrease the content of cations comprising:
   1) a DMSO in liquid state and with a low water content is selected,
   2) this DMSO is placed in contact with a solid consisting of an ion exchange sulphonic resin having its active groups in sulphonic acid ($SO_3H$) form,
   3) the liquid consisting of the purified DMSO with very low contents of cations is then separated from the solid, optionally by filtration, percolation or centrifugation.

2. Process according to claim 1, wherein the placing in contact of the DMSO at step (b) takes place at a temperature of from 19 to 80° C.

3. Process according to claim 1, wherein the resin is based on a polystyrene-divinylbenzene copolymer.

4. Process according to claim 1, wherein the placing in contact of the DMSO with the solid takes place at a temperature of from 19 to 80° C.

5. Process according to claim 4, wherein the temperature is from 20 to 50° C.

6. Process for the purification of dimethyl sulphoxide (DMSO) to decrease the content of metal cations therein, comprising:
   (a) a DMSO in liquid state and with a low water content of less or equal to 0.15% by weight is selected,
   (b) this DMSO is placed in contact with a solid consisting of an ion exchange sulphonic resin having its active groups in sulphonic acid (SO3H) form, this resin being based on a polystyrene-divinyl benzene copolymer in which the divinylbenzene represents from 50 to 60% by weight of the copolymer, and
   (c) the liquid consisting of the purified DMSO with very low contents of metal cations is then separated from the solid, optionally by filtration, percolation or centrifugation.

* * * * *

UNITED STATES PATENT AND TRADEMARK OFFICE
CERTIFICATE OF CORRECTION

PATENT NO. : 5,990,356
DATED : November 23, 1999
INVENTOR(S) : Annie COMMARIEU, et al.

It is certified that error appears in the above-identified patent and that said Letters Patent is hereby corrected as shown below:

Claim 1, line 1, delete "dimethy" and insert --dimethyl--
Claim 1, line 2, before "cations" insert --metal--
Claim 1, line 9, before "cations" insert --metal--

Signed and Sealed this

Seventeenth Day of October, 2000

Attest:

Q. TODD DICKINSON

*Attesting Officer*     *Director of Patents and Trademarks*